(12) United States Patent
Peterson

(10) Patent No.: US 8,445,739 B2
(45) Date of Patent: May 21, 2013

(54) PROCESS FOR THE CONVERSION OF NATURAL GAS TO ACETYLENE AND LIQUID FUELS WITH EXTERNALLY DERIVED HYDROGEN

(75) Inventor: Edward R. Peterson, Pearland, TX (US)

(73) Assignee: Synfuels International, Inc., Dallas, TX (US)

( * ) Notice: Subject to any disclaimer, the term of this patent is extended or adjusted under 35 U.S.C. 154(b) by 742 days.

(21) Appl. No.: 12/548,725

(22) Filed: Aug. 27, 2009

(65) Prior Publication Data

US 2011/0054231 A1 Mar. 3, 2011

(51) Int. Cl.
*C07C 2/78* (2006.01)
(52) U.S. Cl.
USPC .......... 585/540; 585/251; 585/534; 585/538; 585/539
(58) Field of Classification Search
None
See application file for complete search history.

(56) References Cited

U.S. PATENT DOCUMENTS

| 6,323,247 | B1 * | 11/2001 | Hall et al. ..................... 518/700 |
| 2005/0065392 | A1 | 3/2005 | Peterson et al. |
| 2007/0191655 | A1 | 8/2007 | Peterson et al. |

OTHER PUBLICATIONS

International Search Report, International Application No. PCT/US2009/055325, dated Aug. 27, 2010.
Australian Office Action dated Nov. 9, 2012 for corresponding Australian Application No. 2009351655 (2 pgs.).

* cited by examiner

*Primary Examiner* — Tam M Nguyen
(74) *Attorney, Agent, or Firm* — Timothy S. Westby; Porter Hedges LLP

(57) ABSTRACT

A process for converting natural gas from which contaminants have been sufficiently removed to acetylene includes heating the purified gas through a selected range of temperature for adequate time or combustion of the purified gas at adequate temperature within a suitable environment during an adequate reaction time to convert a fraction of the gas stream to acetylene, wherein the acetylene is directed for other processes, reactions, and uses. A process for converting natural gas to liquid hydrocarbons by combusting externally derived hydrogen for heating natural gas to a selected range of temperature. A process for converting natural gas to liquid hydrocarbons by reacting conversion products with externally derived hydrogen to form olefins comprising ethylene, and catalytically forming liquid hydrocarbons from the olefins comprising ethylene.

20 Claims, 6 Drawing Sheets

PROCESS FOR THE CONVERSION OF NATURAL GAS TO ACETYLENE AND LIQUID FUELS WITH EXTERNALLY DERIVED HYDROGEN

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

This invention pertains to conversion of natural gas to acetylene. More particularly, natural gas is converted to reactive hydrocarbons comprising acetylene with externally derived hydrogen sources and the reactive hydrocarbons are reacted to form hydrocarbon liquids.

2. Description of Related Art

Conversion of natural gas into hydrocarbon liquids has been a technological goal for many years. The goal has become even more important in recent years as more natural gas has been found in remote locations, where gas pipelines may not be economically justified. A significant portion of the world reserves of natural gas occurs in such remote regions. While liquefied natural gas (LNG) and methanol projects have long attracted attention by making possible conversion of natural gas to a liquid, in recent years the advent of large scale projects based upon Fisher-Tropsch (F-T) technology have attracted more attention.

The conversion of natural gas to unsaturated hydrocarbons and hydrogen by subjecting the hydrocarbons in natural gas to high temperatures produced by electromagnetic radiation or electrical discharges has been extensively studied. U.S. Pat. No. 5,277,773 discloses a conversion process that subjects methane plus hydrocarbons to microwave radiation so as to produce an electric discharge in an electromagnetic field. U.S. Pat. No. 5,131,993 discloses a method for cracking a hydrocarbon material in the presence of a microwave discharge plasma and a carrier gas, such as oxygen, hydrogen and nitrogen, and, generally, a catalyst. U.S. Pat. No. 3,389,189 is an example of patents relating to production of acetylene by an electric arc.

Methane pyrolysis to acetylene by rapid heating in a reaction zone and subsequent rapid quenching has also been extensively investigated. Subatmospheric pressures and specific ranges of velocities of hydrocarbon gases through the reaction zone are disclosed in U.S. Pat. No. 3,156,733. Heat is supplied by burning of hydrocarbons.

In particular, we refer to U.S. Pat. Nos. 6,130,260; 6,323,247 and 6,602,920 by Hall et al. Hall et al. do not claim or disclose separation and isolation of the acetylene from the other gas components prior to hydrogenation. We provide a process step whereby the acetylene is selectively separated from the other gas components prior to hydrogenation, and directed as a discrete product stream. This reduces the amount of gas, such as ethylene, that must be treated in the hydrogenation step. The ethylene may be removed from this hydrogenation stream and combined with the product stream of the hydrogenator thus increasing overall yield of acetylene in a discrete product stream. Hall et al. do not separate ethylene from any stream for recycling to form acetylene.

Although the prior art has disclosed a range of methods for forming acetylene from natural gas, an energy-efficient process for converting natural gas to an isolated acetylene product has not been available.

SUMMARY OF THE INVENTION

Accordingly, a method for converting natural gas to an acetylene stream comprises the steps of providing a stream of natural gas, separating the natural gas stream into at least a feed stream and a burn stream, wherein the burn stream at least partially combusted, and wherein the feed stream is heated by the combustion to a temperature for adequate time such that reactive products are formed comprising a preferably acetylene portion, quenching the reaction, and separating the remaining products from an acetylene portion.

The pressure of the natural gas stream may be between about 1 bar and about 20 bars. The feed stream may be heated to a temperature of from about 1000 K to about 1800 K, and the feed stream may be maintained at a temperature of at least 1000 K for a period of from about 0.1 to about 100 milliseconds and the feed stream is preferably maintained at a temperature of at least 1000 K for a period of from about 0.2 to about 10 milliseconds.

A method for converting natural gas to hydrocarbon liquids by combusting an externally derived hydrogen stream, thereby converting at least a portion of the natural gas in a conversion reactor, wherein the conversion reactor is at least partially heated to conversion conditions by combusting a hydrogen stream, such that that olefins are produced, and converting at least a portion of the olefins to hydrocarbon liquids.

A method for converting natural gas to liquid hydrocarbons with an externally derived hydrocarbon stream comprises the steps of forming an acetylene stream by directing a natural gas stream to a conversion reactor, separating the natural gas stream into at least a feed stream and a burn stream, wherein the burn stream is at least partially combusted, and wherein the feed stream is heated by the combustion to a temperature for adequate time such that reactive products are formed comprising a preferably acetylene portion, hydrogenating the acetylene portion in contact with externally derived hydrogen to form ethylene portion, and reacting the ethylene portion to form a liquid hydrocarbon product.

The method for converting natural gas to liquid hydrocarbons with hydrogen derived from a commercial source such as a pipeline or storage facility or at least one of the processes chosen from gasifying a biomaterial, producing syngas, collecting Fischer-Tropsch tail gases, electrolyzing hydrogen containing chemicals such as hydrogen chloride and water, and combinations thereof.

DETAILED DESCRIPTION OF THE PREFERRED EMBODIMENTS

Figure 1:
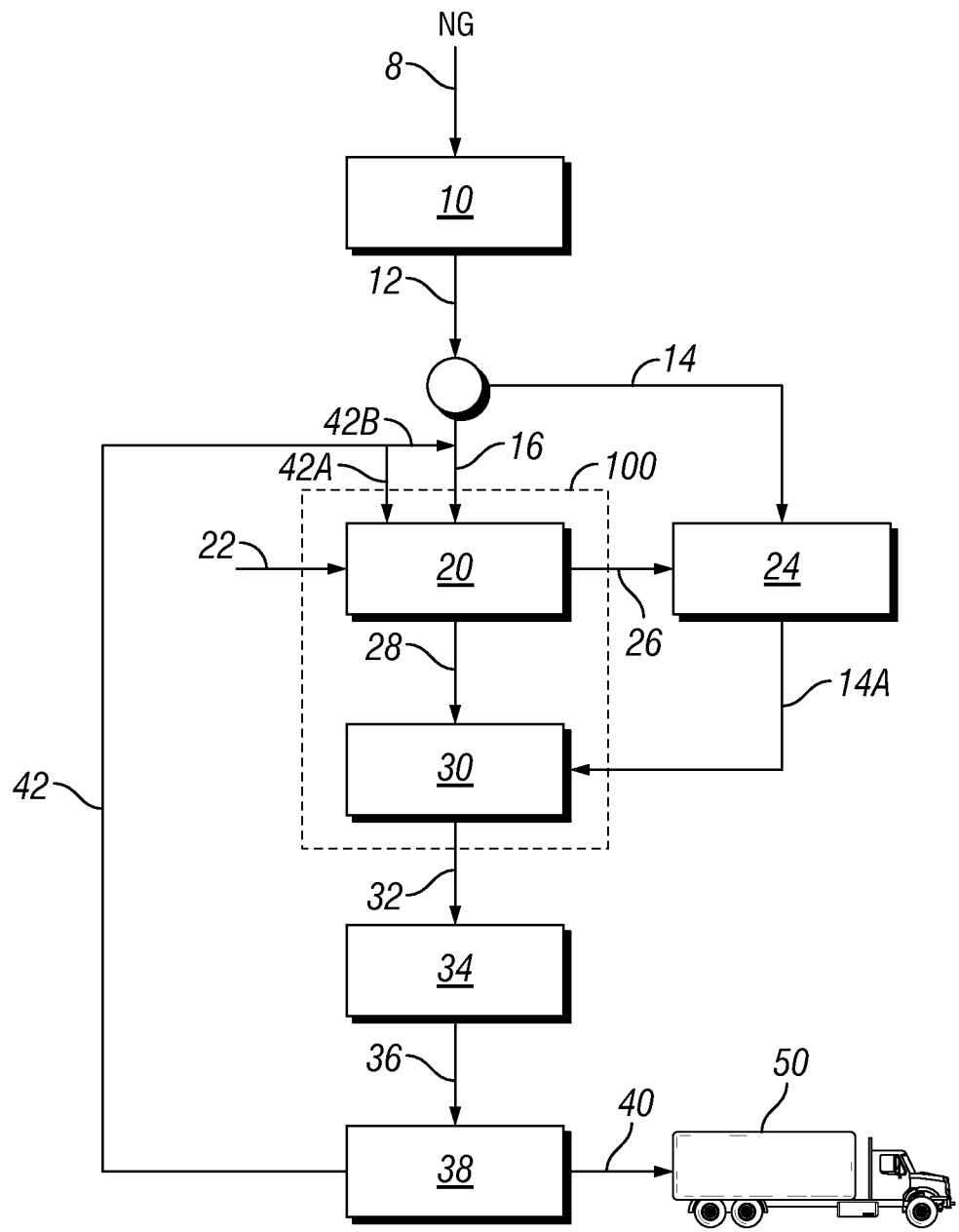
FIG. 1 shows an exemplary process diagram wherein a portion of the natural gas is converted to form acetylene, and a non-acetylene product stream is recycled.

FIG. 1 illustrates an example of the steps for producing acetylene or an acetylene stream from natural gas for downstream processes. Exemplary processes include conversion to a liquid product such as naphtha, diesel, kerosene, or gasoline. Natural gas, hereinafter NG, may be from any form of natural gas, without limitation. In the disclosed process, inlet stream 8 comprising NG, contains impurities and contaminants. NG contaminant removal processes 10 produce feed stream 12, comprising cleaned NG. Feed stream 12 comprises NG, with contaminants, such as sulfur or nitrogen. Feed stream 12 is split into reaction stream 14 and burn stream 16.

In instances, burn stream 16 comprises a diverted portion of feed stream 12. Burn stream 16 is optionally delivered to an in-line burner 20. Diverted portion 12 of the NG is combusted in burner 20. Alternatively, a portion of NG in burn stream 16 is combusted in burner 20. Burner 20 combustion temperature of burn stream 16 is preferably between 1000 and 2800 K. In instances, burner 20 comprises air, oxygen or combinations thereof for combusting burn stream 16. Addition of water or steam to the burner 20 may be used to lower and thereby control the combustion temperature. In certain instances, the combustion in burner 20 is controlled with supplemental stream 22. Supplemental gas stream 22 comprises gases for reduction of combustion or process related pollutants or byproducts, for instance, oxygen enriched air, steam, carbon dioxide, carbon monoxide, hydrogen, exhaust gases, ethylene, unreacted NG and combinations thereof. In certain instance, supplemental gas stream 22 further comprises gases, liquids, or solids suitable for combustion in burner 20. Further pollutants are controlled preferably with oxygen enriched air such that NOx production from burner 20 is decreased. Combustion products, unburned NG, and other exhaust components are removed from burner 20 via burner product stream 28.

As shown in FIG. 1, a portion of inlet gas stream 12 is separated into reactor stream 14. Reactor stream 14 is conveyed to preheater 24. In certain instances, preheater 24 is at least partially heated by burner gas stream 26. Reactor stream 14 is preferably pre-heated in pre-heaters 14. Alternatively, preheater 24 is heated by alternate thermal sources, for instance, steam, heat exchangers, thermal recycling, or solar heating. Preheater 24 is optionally excluded from reactor stream 14. Reactor stream 14 is directed to reactor 30 as reaction stream 14A. Reaction stream 14A comprises the reactor feed stream. Reaction stream 14A is directed to a reactor 30.

Reactor 30 is in thermal communication with burner 20. Alternatively, reactor 30 and burner 20 form reaction section 100. Reaction stream 14A comprising NG feeds reactor 30. Reactor 30 is heated to a reaction temperature by direct heat exchange through burner product stream 28. Alternatively, reactor 30 is in thermal coupling with burner 20, or burner product stream 28. Thermal coupling further comprises heat exchange or thermal recycling between burner 20 and reactor 30. In certain instances, burner product stream 28 is mixed with reaction stream 14A prior to, during, or after introduction to reactor 30. Burner product stream 28 preferably raises temperature of reactor 30 to between about 800 K and about 3000 K, preferable between about 1000K and about 2800K. In alternate configurations the temperature of reactor 30 is between about 1000K and 2000K. Further, the temperature of the reactor 30 is controlled to favor reaction kinetics towards production of acetylene. In particular, "lean" natural gas, i.e., gas with 95% or greater methane reacts to mostly acetylene. Where the natural gas is lean, it is desirable to operate the reactor in the upper end of the desired temperature range to achieve a higher content of alkynes, especially acetylene. In contrast, in a richer stream, it may be desirable to operate at a temperature lower in the desirable range to achieve a higher content of alkynes, especially acetylene. Addition of water or steam to the burner 30 may be used to control the reactor 30 temperature. Reactor 30 is configured to mix reactor burner product stream 28 and reaction stream 14A at elevated temperature to form reactor product stream 32. Reactor product stream 32 preferably comprises acetylene; preferably comprises a concentration of more than about 5% acetylene by volume. In certain instances, reactor product stream 32 comprises ethylene, ethane, other reactive compounds, hydrocarbons, and combinations thereof.

Additionally, residence time of reaction stream 14A in reactor 30 is controlled to preferably convert reaction stream 14A, comprising NG, to acetylene. As described hereinabove, reactor 30 further comprises burner product stream 28. In certain instances, ethylene, hydrocarbons, and other reactive compounds comprise at least a portion of reactor product stream 32 regardless of residence time. Preferably, ethylene, hydrocarbons, and other reactive compounds comprise a concentration less than about 95% of the reactor product stream 32 by volume. Alternatively, residence time of burner product stream 28 and reaction stream 14A in the reactor 30 is controlled to prevent further reactions. For instance, controlling or minimizing further reactions increases production of acetylene in reactor product stream 32. Control of residence time in reactor 30 is further configured to minimize coke formation. The residence time is less than about 100 milliseconds; alternatively less than about 80 milliseconds. In further instances, residence times are longer than about 0.1 milliseconds; alternatively longer than about 0.5 milliseconds. In certain instances, a shorter residence time is preferred for converting NG to acetylene, and minimizing production of ethylene, hydrocarbons, and other reactive products. Shorter residence times are preferable for increasing acetylene concentration in reactor product stream 32. Further, the pressure of the burn stream 16 is maintained between about 1 bar and about 20 bars for maintaining conversion efficiency of reactor. Alternatively, the reaction stream 14A is maintained between about 1 bar and about 20 bars to preferably produce reactor product stream 32 comprising primarily acetylene. The reactor product stream 32 further comprises combustion products, for instance, those found in burner product stream 28 and any unconverted feed, for instance, reaction stream 14A comprising NG.

The reaction duration is further limited by a quench 34. To stop the reactions and prevent the reverse reactions or further reactions to form carbon and other hydrocarbon compounds, rapid cooling or "quenching" is essential, typically in 1 to 100 milliseconds. Further, the quench in quench system 34 may be achieved by spraying water, oil, solvent or other compatible liquid into reactor quench chamber. Alternatively, the quench 34 is conveyed through or into water, natural gas feed, or compatible liquids; or expanded in a kinetic energy quench such as a Joule Thompson expander, choke nozzle or turbo expander. Quench 34 comprises introducing a fluid, such as a heavy hydrocarbon, an inorganic liquid, acetylene solvent, water or steam, or another fluid to the reactor product stream 32. Quench 34 comprises the liquid introduction in sufficient quantity to abate ongoing reactions in reactor product stream 32. Further, quench 34 is introduced to reactor product stream 32 as a means to maximize acetylene concentration by ceasing further reactions, conversions and hydrogenation in reactor product stream 32.

Quenched stream 36 is subjected to acetylene separation 38 such that the acetylene is separated from the quenched stream 36 to form acetylene stream 40 and recycle stream 42. Acetylene stream 40 is conveyed, or transported to additional reactors for further reactions. Exemplary reactions include, but are not limited to, polymer synthesis, aldehyde synthesis, welding gas synthesis, and liquid hydrocarbon synthesis. Alternatively, acetylene stream 40 is collected for transport 50.

Recycle stream 42 is directed to the burner 20. Without limitation by theory, recycle stream 42 comprises ethylene, hydrogen, and un-reacted burner product gases (similar to burner product stream 28), for instance carbon dioxide, carbon monoxide, methane, ethane, sulfur dioxides, nitrous oxides, and the like without limitation. Recycle stream 42 is configured to reduce certain emissions, for instance oxides of sulfur or oxides of nitrogen. Further, recycle stream 42 introduced to burner 20 comprises a means to increase efficiency in the conversion of NG to form acetylene stream 40.

Direct recycle stream 42A is introduced to burner 20 directly. Direct recycle stream 42A is introduced as a means to control combustion in burner 20. Alternatively, direct recycle stream 42A is combusted to reduce the amount of burner feed 16, comprising NG. In instances, direct recycle stream 42A increases the NG available for reactor stream 14, conversion, and for forming acetylene stream 40. In further alternate configurations, direct recycle stream 42A is a supplemental gas stream 22 component. Alternatively, supplemental gas stream 22 comprises direct recycle stream 42A.

Alternatively, a heater recycle stream 42B is configured for preheating the burner feed 16. Heater recycle stream 42B increases the temperature of burner feed 16. Heater recycle stream 42B as introduced to burner 20 reduces burner feed 16, comprising NG, to control and maintain reaction temperature. Heater recycle stream 42B reduces certain emissions, for instance oxides of sulfur or oxides of nitrogen, by raising the temperature of burner feed 16 prior to introduction to burner 20. Further, heater recycle stream 42B introduced to burner 20 comprises a means to increase efficiency in the conversion of NG to form acetylene stream 40, by decreasing the burner feed 16, comprising NG. Without limitation by theory, heater recycle stream 42B increases the NG available for reactor stream 14, conversion, and for forming acetylene stream 40.

Figure 2:
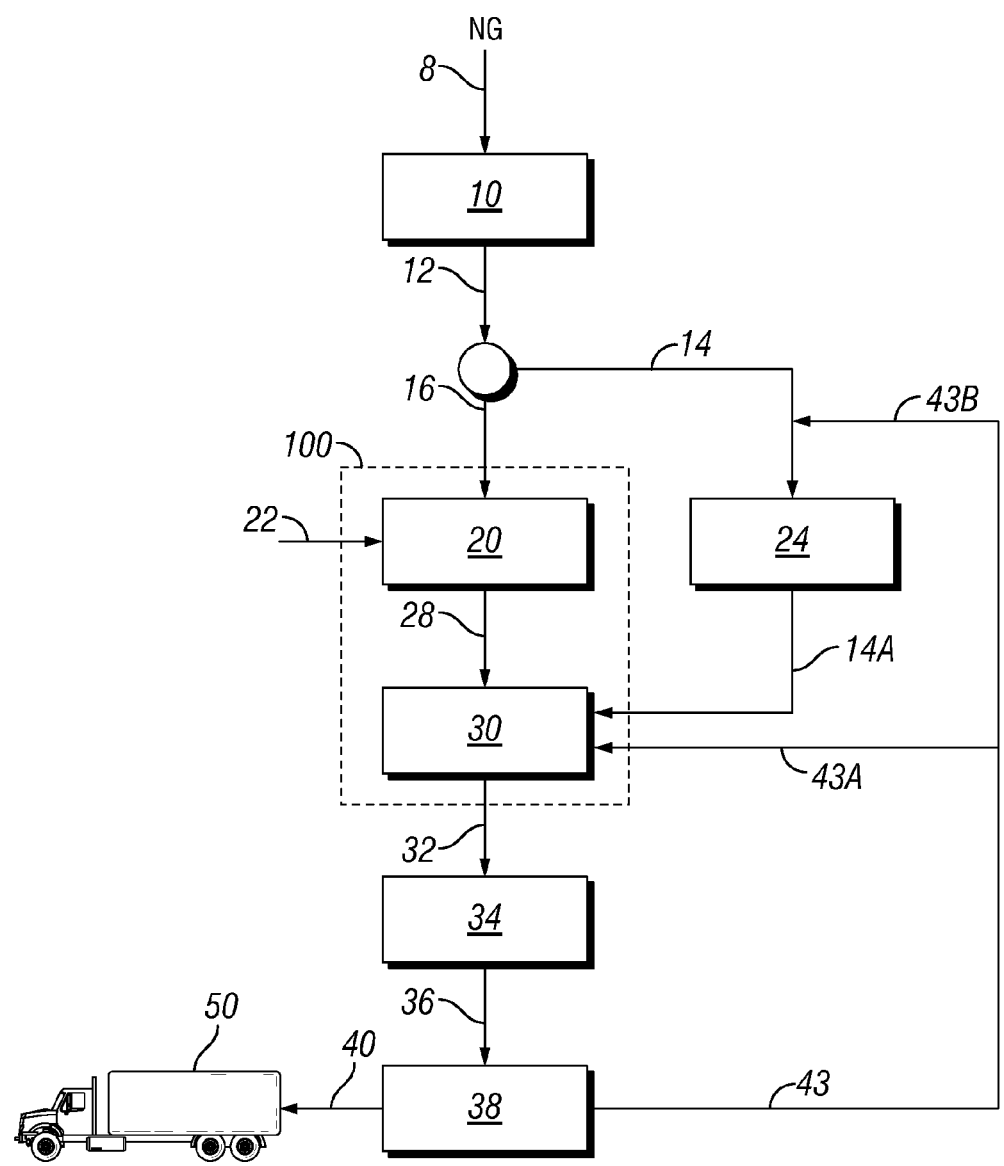
FIG. 2 shows an exemplary process diagram wherein a portion of the natural gas is converted to form acetylene and a non acetylene product stream comprising ethylene is recycled.

Referring to FIG. 2, recycle stream 43 is directed to the reactor 30. Recycle stream 43A introduced to reactor 30 reduces the amount of burner product stream 28, introduced into reactor 30. Further, recycle stream 43 introduced to reactor 30 comprises convertible ethylene. The introduction of ethylene into reactor 30 under reaction conditions comprises a means to increase concentration of acetylene in acetylene stream 40. Recycle stream 43 is alternately directed to reactor 30 via reactor stream 14.

Direct recycle stream 43A is an inlet stream to reactor 30. Direct recycle stream 43A comprises ethylene and without limitation by theory, converts at least in part to acetylene under reactor conditions. Alternatively, direct recycle stream 43A comprising ethylene pushes reaction kinetics in reactor 30 toward the production of acetylene. Further, direct recycle stream 43A comprises compounds and molecules similar to burner product stream 28. Direct recycle stream 43A and burner product stream 28 comprise additional reactants to form acetylene. Further, direct recycle stream 43A may rearrange and re-associate with portions of burner product stream 28, such that these compounds are removable from acetylene stream 40.

In certain configurations, heater recycle stream 43B is configured for preheating the reactor stream 14. In configurations, heater recycle stream 43B is mixed with reactor stream 14, to form preheated reaction stream 14A. Heater recycle stream 43B mixing with reactor stream 14 is configurable to replace preheater 24. Alternatively, preheater 24 is a mixing point of heater recycle stream 43B with reactor stream 14 to form reaction stream 14A. In certain instances, heater recycle stream 43B is introduced into reaction stream 14A after preheater 24. Further, heater recycle stream 43B introduced to reactor 30 comprises a portion of ethylene. The introduction of ethylene into reactor 30 under reaction conditions comprises a means to increase concentration of acetylene in acetylene stream 40. Further, introduction of heater recycle stream 43B to reactor 30, increases operating efficiency of reactor 30 by maintaining preferred reactor conditions.

Figure 3:
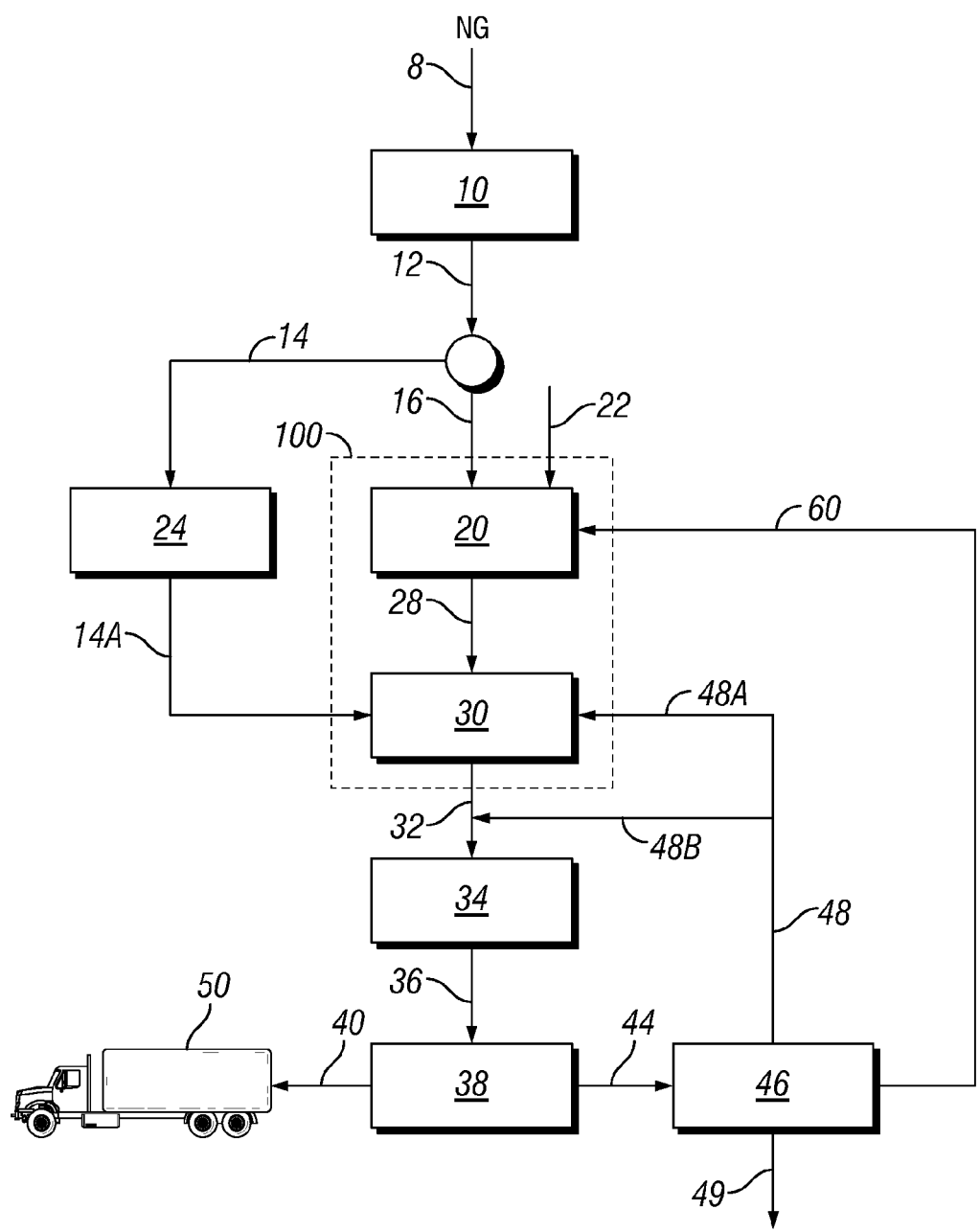
FIG. 3 shows an exemplary process diagram wherein a portion of the natural gas is converted to form acetylene, and product streams, including a non-acetylene product stream and an ethylene product stream, are recycled.

Referring now to FIG. 3, recycle stream 44 comprising ethylene is directed to separator 46. In certain arrangements, separator 46 is configured for the isolation and separation of ethylene from recycle stream 44. In certain instances, separator 46 comprises a conventional means including, but not limited to, pressure swing absorption, membrane separation, cryogenic processing, or other gas separation techniques commonly practiced by those skilled in the art. Further, separator 46 forms ethylene stream 48 and remainder stream 60. In certain instances, remainder stream 60 comprises hydrogen and un-reacted burner product gases, for instance carbon dioxide, carbon monoxide, methane, ethane, sulfur dioxides, nitrous oxides, and the like without limitation. As such, separator 46 removes compounds comprising hydrogen and un-reacted burner product gases, to form an ethylene stream 48. Ethylene stream 48 is directed to the reactor 30. Alternately, ethylene stream 48 is directed to reactor products stream 32. Alternately, ethylene is collected as a pure or impure product stream 49, for further processing.

In certain instance, reactor ethylene stream 48A is fed directly to the reactor 30. Reactor ethylene stream 48A comprises ethylene and without limitation by theory, preferably converts to acetylene under reactor conditions. Further, reactor ethylene stream 48A comprises ethylene at an elevated temperature as an additional reactant for conversion to acetylene. Further, reactor ethylene stream 48A may rearrange, re-associate, and convert portions of reaction stream 14 to acetylene more readily. In instances these reactions increase the acetylene concentration in reactor product stream 32 and later, acetylene stream 40. Preferably, the introduction of ethylene into reactor 30 under reaction conditions comprises a means to increase concentration of acetylene in acetylene stream 40.

In certain instances, quench ethylene stream 48B is mixed with reactor products stream 32. Quench ethylene stream 48B comprises ethylene and without limitation by theory, preferably converts to acetylene under conditions found in reactor products stream 32. Further, quench ethylene stream 48B comprises ethylene at an elevated temperature to provide additional conversion to acetylene. Quench ethylene stream 48B may rearrange, re-associate, and convert portions of reactor product stream 32 to acetylene more readily. In instances, quench ethylene stream 48B is used to simultaneously increase acetylene production, as described, and to initiate the quenching of further reactions. Without limitations, the quench ethylene stream reactions increase the acetylene concentration in reactor product stream 32 and later, acetylene stream 40. Preferably, the introduction of quench ethylene stream 48B also reduces further reactions and thus comprises a means to increase the concentration of acetylene in acetylene stream 40.

As separator 46 removes the ethylene portion of recycle stream 44, via ethylene stream 48, the remainder stream 60 is formed. Remainder stream 60 comprises hydrogen and unreacted burner product gases, for instance carbon dioxide, carbon monoxide, sulfur dioxides, nitrous oxides, and the like, without limitation. As such, separator 46 removes compounds comprising hydrogen and un-reacted burner product gases that may be recycled to burner 20. In certain instances, remainder stream 60 is directed to burner 20. Further, remainder stream 60 introduced to burner 20 comprises a means to increase efficiency in the conversion of NG to form acetylene stream 40 for transport 50. In certain instances, remainder stream is introduced to burner 20 directly as a means to control combustion in burner 20. Alternately, remainder stream 60 is a portion of supplemental gas stream 22 to burner 20. Remainder stream 60 is used to reduce the amount of burner feed 16, comprising NG. Remainder stream 60 recycled to burner 20 raises the temperature of burner feed 16 prior to introduction to burner 20. Without limitation by theory, remainder stream 60 reduces certain emissions, for instance oxides of sulfur or oxides of nitrogen, by increasing the temperature of burner feed 16. Additionally, remainder stream 60 increases the quantity NG available for reactor stream 14, conversion, and for forming acetylene stream 40.

In alternate configurations, remainder stream 60 comprising hydrogen, a portion of which can be used to generate electricity in an electrical generator, or a portion of which can be used in subsequent chemical processing, is further separated for additional processing. In certain instances, remainder stream 60 is used for alternate reactions. Alternate reactions wherein the desired products from this series of reactions are ethylene and acetylene and most preferably acetylene. Suppression of production of other components may be required to achieve the increased acetylene concentration. This may be accomplished by such methods as adjusting the reaction temperature and pressure, and/or quenching after a sufficiently short residence time, as discussed hereinabove.

Referring to the exemplary process illustrations contained in FIGS. 1, 2, and 3, acetylene separation 38 comprises any means known to one skilled in the art for isolating acetylene. In certain instances, the isolation process comprises adsorption, absorption, distillation, selective membrane permeation, pressure swing absorption, or other gas separation techniques known to those skilled in the art. Further, acetylene separation 38 may comprise introducing additives, supplements, stabilizers, and the like without limitation to the separated acetylene. Further, the acetylene separation 38 forms acetylene stream 40, that has a gas concentration of at least about 30% by volume; alternatively, at least 50% by volume; further, at least about 75% acetylene gas concentration by volume. Preferably, for transportation 50 to other processes, the gas concentration is at least 90% by volume.

Further, referring to the exemplary process illustrations contained in FIGS. 1, 2, and 3, any combination of these steps may be combined. For example, separator 46 created remainder stream 60 in FIG. 3, is configurable for combination with burner recycle stream 42A as illustrated in FIG. 1. Additionally, ethylene stream 48 from separator 46 may be configured to supplement direct recycle stream 42A, burner recycle stream 42B, or combinations thereof as illustrated in FIG. 1. Alternatively, the remainder stream 60 may be configured for return to the acetylene separation 38, quench 34, or the reactor 30 to move reaction kinetics toward higher production of acetylene.

Carbon monoxide may be formed when insufficient oxygen is introduced to burner 20, such that complete combustion of burner stream 16 is not possible. In certain instances, if formed, carbon monoxide may be separated downstream, and later combined in part or whole with the supplemental gas stream 22. Carbon monoxide application in the system in this manner may supply additional energy to the combustion process that would otherwise not be available, and may provide a source of control for the combustion and temperature of the burn stream 16. Without limitation, the combustion of carbon monoxide will, in general, deliver lower thermal energy to the combustion process than burn stream 16, supplemental gas 22 components or components from acetylene separator 38, ethylene separator 46, and the recycle streams associated therewith. Carbon monoxide further provides a reactant that will alter and diminish the severity of reaction conditions that lead to coke formation, thus reducing coke formation. Carbon monoxide, vented from burner 20 via burner product stream 28, to reactor 30, controls the reaction kinetics to preferably form acetylene.

Figure 4:
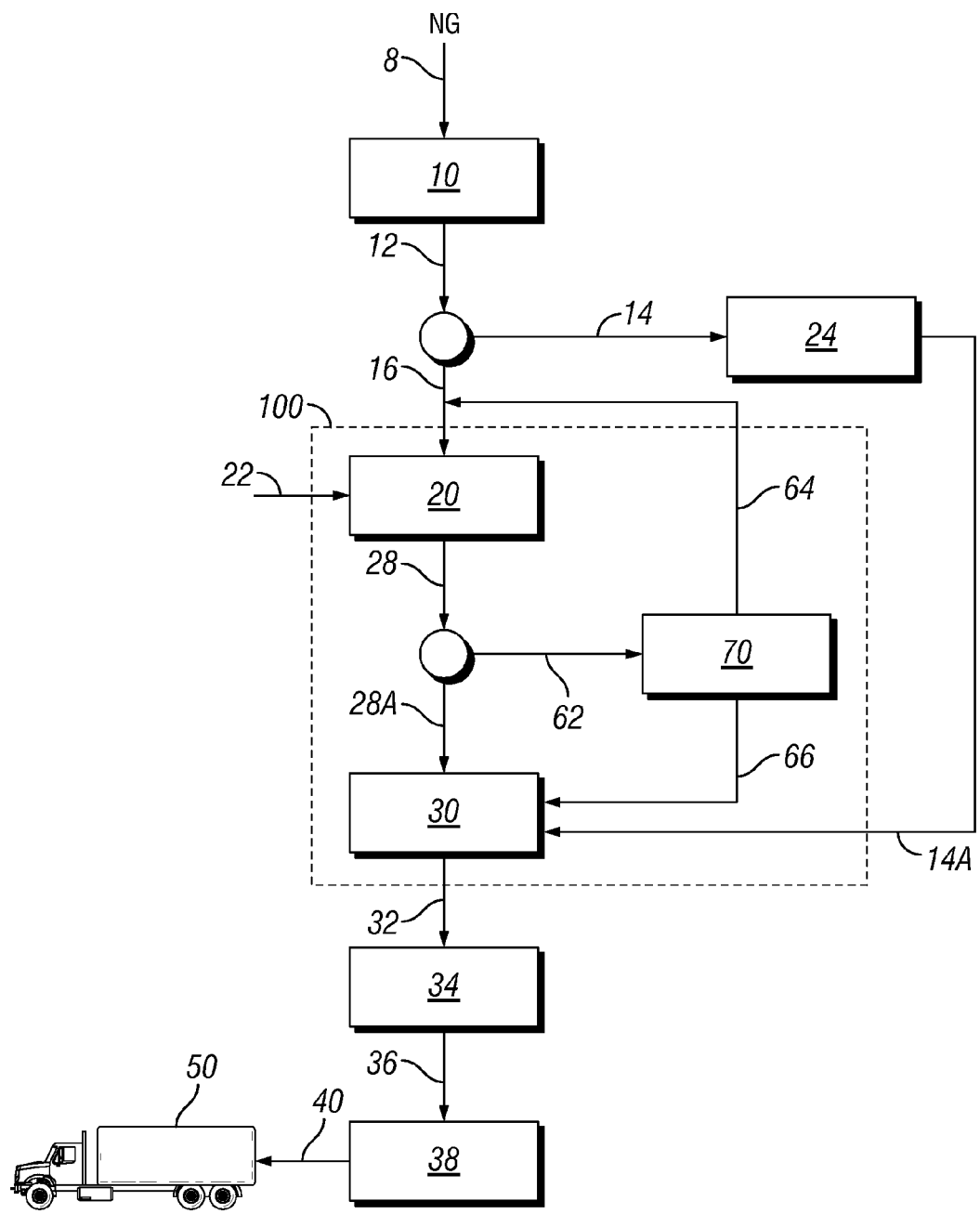
FIG. 4 shows an exemplary process diagram wherein a portion of the natural gas is converted to form acetylene, and a portion of the natural gas is at least partially combusted, wherein the product stream of partially combusted natural gas is recycled

In another alternative configuration, shown in FIG. 4, the burner product stream 28 is at least partially divided. In certain instances, burner-reactor stream 28A is directed to reactor 30 as disclosed herein. Further, a burner product recycle stream 62, produced by the partial combustion of burner stream 16, comprising NG, is directed to an exhaust separator 70. This separation step may be performed according to known methods such as absorption, distillation, selective membrane permeation, pressure swing absorption, or other gas separation techniques known to those skilled in the art.

Exhaust separator 70 is configured to remove certain compounds, for instance without limitation, carbon monoxide, carbon dioxide for a burner control stream 64. Burner control stream 64 configured for introduction to burner 20. Alternatively, burner control stream 64 is mixed with burner stream 16. The burner control stream 64 is a means to control the temperature, combustion, and operation of reactor 30. Additionally, burner separator 70 comprises reactor control stream 66. In certain instances, reactor control stream 66 comprises unburned NG, mixed hydrocarbons, carbon dioxide and water or steam, and depending on the operation conditions, nitrogen and carbon monoxide. In further instances, reactor control stream 66 comprises a portion of ethylene. Reactor control stream 66 may be introduced into reactor 30 as a means to drive reaction kinetics to produce acetylene. Alternatively, at least a portion of burner product stream 62 may be directed to other components of the process, for instance preheater 24, or reactor product stream 32, such that the production of acetylene is favored.

In certain instances, referring to FIG. 3, remainder stream 60, comprising hydrogen, is used as a feed for a fuel cell. Heat generated by the fuel cell may be used to boil the water exiting the fuel cell, forming steam, for introduction to reactor system 100. This steam maybe used to generate, electricity, for instance in a steam turbine. Alternatively, the electricity may be sold, or used to provide heat to preheat the feed, fuel or oxidant, or other equipment, such as, but not limited to, pumps, compressors, fans and other ordinary equipment required to accomplish the goals of the process.

In another configuration, preheater 24 comprises an electrical heater. In certain instances, electric heater derives power from the combustion of any portion of a recycle stream 42 or 43 as illustrated in FIGS. 1 and 2 respectfully. In certain instances, the combustion of recycle streams 42 or 43 is used to power turbine for generating electricity. Preheater 24 is heated by electrical energy such that sufficient thermal energy is provided to raise a sufficient yet controlled temperature for heating reaction stream 14A. Reaction stream 14A is raised to a temperature that is near the conversion temperature, for example as in the reactor 30. Alternatively, an electrical heater provides at least a portion of the thermal energy to reactor for converting the reaction stream 14A to acetylene. Alternatively, the electricity may be sold, or used to provide heat to preheat the feed, fuel or oxidant, or other equipment, such as, but not limited to, pumps, compressors, fans and other ordinary equipment required to accomplish the goals of the process.

Without limitation by theory, the system, including the reactor 30 and ancillary components, as disclosed herein comprises alternative materials. Alternate materials such as tungsten, tantalum, ceramics, or other suitable materials may be used. Further, the reactor 30 may employ in its construction various materials consistent with high temperature processing such as, but not exclusive to tantalum (Ta) or silicon/carbide tubing. As understood, the materials are selected to withstand temperature changes, such as the change in the feed, combustion, or product streams that typically occur in a short period of time.

Without limitation, any component illustrated within the system may be understood to comprise one or more feed streams and one or more product streams. Both feed streams and product streams may employ NG combined with other gas components including, but not limited to, hydrogen, carbon monoxide, ethane, methane, and ethylene. It may also have one or more oxidant feed streams, which employ unequal oxidant concentrations for purposes of temperature or composition control.

The inlet stream 8, comprising NG provided may be sufficiently pure such that contaminant removal 10 is not required, or superfluous to the process. The contaminant removal 10 is configurable for by-passing, skipping, or routing around. In certain instances, the inlet stream 8 may be conducted through the contaminant removal 10 without further processing. The necessity of performing this step or operating the contaminant removal 10 will depend upon the nature of the contaminants, and the intended uses of the acetylene. Further, in certain downstream acetylene synthesis processes, the catalyst used in the catalytic reactor, construction materials used throughout the process, and operating conditions, may impact the operation of the contaminant removal 10.

Note that processing steps may be added after acetylene separation 38 and forming acetylene stream 40. The current disclosure relates to the production of high concentration of acetylene, in acetylene stream 40 for transport 50. Transport 50 comprising directing the acetylene stream to other processes, other facilities, or as a final product. Transport 50 further comprises emulsions or solutions of acetylene in carrier media. In certain instances, acetylene stream 40 is conducted to separate processing for the production of hydrocarbon liquids, such as naphtha or gasoline, or to heavier compounds, such as diesel. In further instances, the acetylene stream 40 is utilized for further synthesis reactions, for example, vinylic compounds, aldehydes, acrylics, and other reactions, without limitation.

Figure 5:
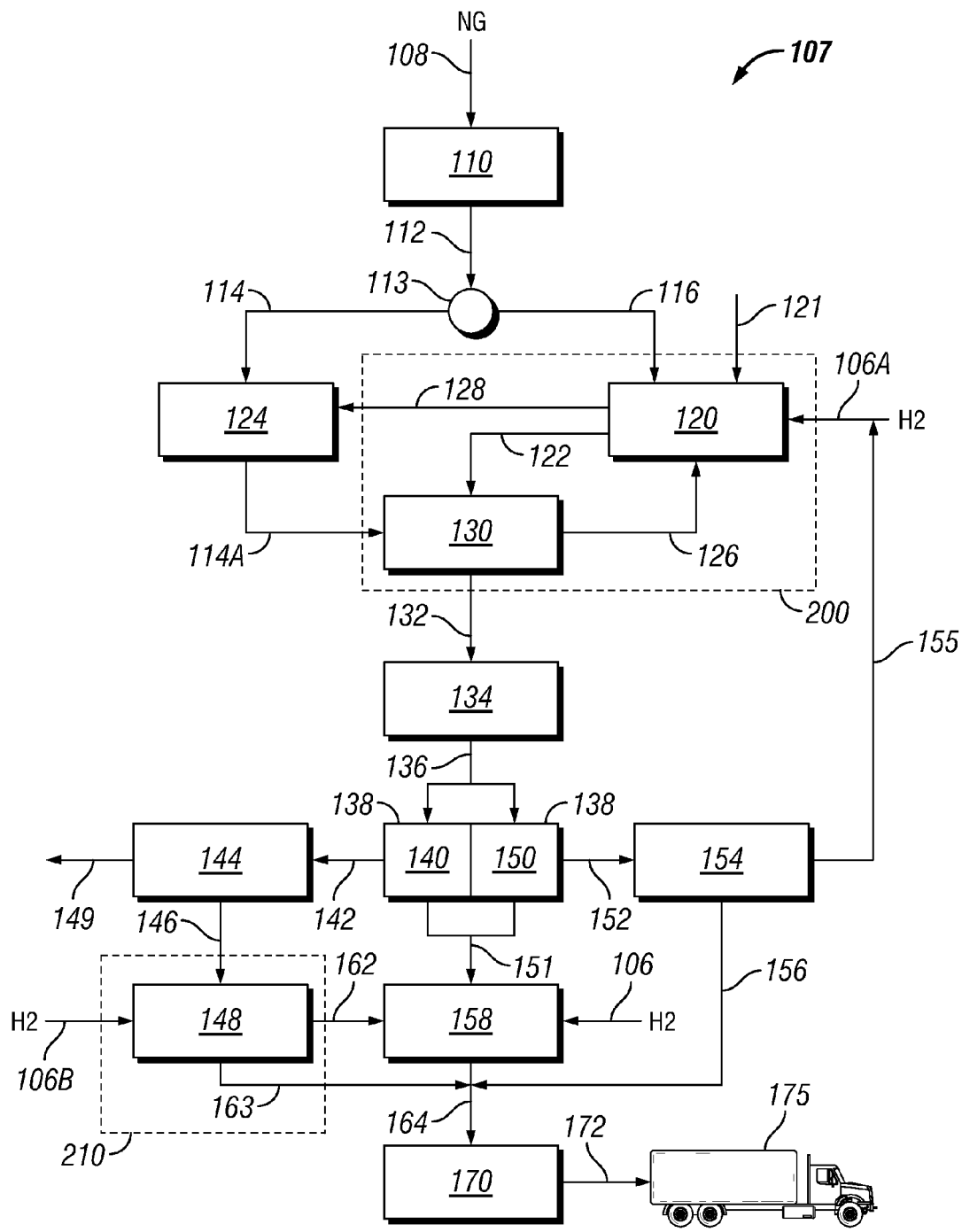
FIG. 5 shows an exemplary process diagram wherein at least one externally derived hydrogen stream is partially combusted to heat a natural gas stream to form conversion products and at least one externally derived hydrogen stream is mixed with the conversion products to form liquid hydrocarbon precursor olefins.

FIG. 5 illustrates a liquid hydrocarbon production system 107. Liquid hydrocarbon system 107 comprises a process to convert natural gas to liquid hydrocarbons in product stream 172. Exemplary processes include conversion to a liquid product such as naphtha, diesel, kerosene, or gasoline. Natural gas, hereinafter NG, may be from any of natural gas, without limitation. In the disclosed process, inlet stream 108 comprising NG, contains impurities and contaminants. NG contaminant removal processes 110 produce feed stream 112, comprising cleaned NG. Feed stream 112 comprises NG, with contaminants, such as sulfur or nitrogen. Feed stream 112 is split into reaction stream 114 and burn stream 116 by control 113.

In instances, burn stream 116 comprises a diverted portion of feed stream 112. Burn stream 116 is delivered to an in-line burner 120. Burn stream 116 is diverted by control 113. Control 113 is configured to divert burn stream 116 from feed stream 112 at an operator specified interval. Control 113 may be configured to divert burn stream 116 from feed stream 112 when insufficient fuel stream 121 is available. Alternatively, control 113 diverts burn stream 116 as a make-up gas when externally derived fuel is not available to achieve a preferred temperature.

Diverted portion of feed stream 112 comprising NG is combusted in burner 120. Alternatively, a portion of NG in burn stream 116 is combusted in burner 120. Burner 120 combustion temperature of burn stream 116 is preferably between 1000 and 2800 K. In instances, burner 120 comprises air, oxygen or combinations thereof for combusting burn stream 116. Addition of water or steam to the burner 120 may be used to lower and thereby control the combustion temperature.

In certain instances, the combustion in burner 120 is controlled with the composition of fuel stream 121. Fuel stream 121 comprises at least one combustible solid, liquid, gas, slurry, or combinations thereof. Further, fuel stream 121 comprises gases for reduction of combustion related pollutants, for instance, oxygen enriched air, steam, carbon dioxide, exhaust gases, and combinations thereof. In certain instance, pollutants are controlled preferably with oxygen enriched air such that NOx production from burner 120 is decreased. Further, combustion products, unburned NG, and other exhaust components are removed from burner 120 via burner product stream 122 or thermal stream 128.

As shown in FIG. 5, a portion of inlet gas stream 112 is separated into reactor stream 114 by control 113. Reactor stream 114 is conveyed to preheater 124. In certain instances, preheater 124 is at least partially heated by burner thermal stream 128. Reactor stream 114 is preferably pre-heated in preheater 124. Alternatively, preheater 124 is heated by alternate thermal sources, for instance, steam, heat exchangers, thermal recycling, or solar heating. Preheater 124 is optionally excluded from reactor stream 114. Reactor stream 114 is directed to reactor 130 as reaction stream 114A. Reaction stream 114A comprises the reactor feed stream. Reaction stream 114A is directed to a reactor 30.

Reactor 130 is in thermal communication with burner 120. Alternatively, reactor 130 and burner 120 form reaction section 200. Reaction stream 114A comprising NG feeds reactor 130. Reactor 130 is heated to a reaction temperature by direct heat exchange through burner product stream 122. Alternatively, reactor 130 is in thermal coupling with burner 120, or burner product stream 122. Thermal coupling further comprises heat exchange or thermal recycling between burner 120 and reactor 130. In certain instances, burner product stream 122 is mixed with reaction stream 114A prior to, during, or after introduction to reactor 130. Reactor 130 is configured to mix and reactor burner product stream 122 and reaction stream 114A at elevated temperature to form reactor product stream 132. Reactor product stream 132 preferably comprises acetylene, ethylene, olefins and other hydrocarbons. In certain instances, reactor product stream 132 comprises ethylene, ethane, other reactive compounds, hydrocarbons, and combinations thereof.

Further, reactor 130 produces reactor recycle stream 126 comprising unreacted gases, waste gases, exhaust gases, and other gases not favorable for the production of liquid hydrocarbons. In certain instances, reactor recycle stream 126 is separated, filtered, modified, or treated by any means known to one skilled in the art. Further, reactor recycle stream 126 is recycled to burner 120. Without limitation by theory, recycle stream 126 replaces NG in burner feed stream 116, increasing liquid hydrocarbon production and through put in system 107. Combustion of reactor recycle stream 126 comprises a means to regulate and control temperature of reactor 130.

Burner product stream 122 preferably raises temperature of reactor 130 to between about 800 K and about 3000 K, preferable between about 1000K and about 2800K. In alternate configurations the temperature of reactor 130 is between about 1000K and 2000K. Further, the temperature of reactor 130 is controlled to favor reaction kinetics towards production of acetylene, ethylene, and olefin hydrocarbons, without limitation. In particular, "lean" natural gas, i.e., gas with 95% or greater methane reacts to mostly acetylene. Where the natural gas is lean, it is desirable to operate reactor 130 in the upper end of the desired temperature range to achieve a higher content of alkynes, especially acetylene. In further instances, where the natural gas is lean, operation of the reactor 130 at lower end of the temperature ranges is configurable to preferably produce ethylene. In contrast, in a richer stream, it may be desirable to operate at a temperature lower in the desirable range to achieve a higher content of alkynes. Operation at the higher end of the temperature range in this instance may be preferable for the production of ethylene and other olefins, or other reactive products. Addition of water or steam to burner 120 via fuel stream 121 may be used to control to the reactor 130 temperature.

Suppression of the production of other components in product stream 132 may be required to achieve the product stream 132 composition. This may be accomplished by such methods as adjusting the reaction temperature and pressure, and/or quenching after a desired residence time. It is preferred to maintain the pressure of the natural gas within the reactor 130 to between 1 and 20 bar (100-2000 kPa) to achieve the preferred reactive products. Additionally, residence time of reaction stream 114A in the reactor 130 is controlled to preferably convert reaction stream 114A, comprising NG, to acetylene, ethylene, olefins, and other hydrocarbons. As described hereinabove, reactor 130 further comprises burner product stream 122. In certain instances, ethylene, hydrocarbons, and other reactive compounds comprise at least a portion of reactor product stream 132 regardless of residence time. Preferably, ethylene, olefinic hydrocarbons, and other reactive compounds comprise a concentration less than about 50% of the reactor product stream 132 by volume. Alternatively, residence time of burner product stream 128 and reaction stream 114A in the reactor 30 is controlled to prevent further reactions. For instance, controlling or minimizing further reactions increases production of acetylene, ethylene, and olefins in reactor product stream 132. Control of residence time in reactor 130 is further configured to minimize coke formation. The residence time is less than about 100 milliseconds; alternatively less than about 80 milliseconds. In further instances, residence times are longer than about 0.1 milliseconds; alternatively longer than about 0.5 milliseconds. In certain instances, a shorter residence time is preferred for converting NG to acetylene, and minimizing production of ethylene, hydrocarbons, and other reactive products. Shorter residence times are preferably for increasing acetylene concentration in reactor product stream 132. Longer residence times are favorable for producing olefins and other hydrocarbons. Further, the pressure of burn stream 116 is maintained between about 1 bar and about 20 bars for maintaining conversion efficiency of reactor 130. Alternatively, reaction stream 114A is maintained between about 1 bar and about 20 bars to preferably produce reactor product stream 132 comprising primarily acetylene and ethylene as reactive hydrocarbons. The reactor product stream 132 further comprises combustion products, for instance, those found in burner product stream 122 and any unconverted feed, for instance, reaction stream 114A comprising NG.

The reaction duration is further limited by a quench 134. To stop the reactions and prevent the reverse reactions or farther reactions to form carbon and other hydrocarbon compounds, rapid cooling or "quenching" is essential, typically in 1 to 100 milliseconds. Further, the quench in quench system 134 may be achieved by spraying water, oil, or liquid product into reactor quench chamber. Alternatively, the quench 134 is conveyed through or into water, natural gas feed, or liquid products; or expanded in a kinetic energy quench such as a Joule Thompson expander, choke nozzle or turbo expander. Quench 134 is configurable to preheat other streams within the liquid hydrocarbon system 107, without limitation. Quench 134 comprises introducing a fluid, such as a heavy hydrocarbon, an inorganic liquid, water or steam, or another fluid to the reactor product stream 132. Quench 134 comprises the liquid introduction in sufficient quantity to abate ongoing reactions in reactor product stream 132. Further, quench 134 is introduced to reactor product stream 132 as a means to maximize acetylene, ethylene, and other olefin concentrations by ceasing further reactions, conversions and hydrogenation in reactor product stream 132. A15

Quenched stream 136 is direct to a dual separator 138, comprising a carbon dioxide ($CO_2$) separator 140 and a hydrocarbon separator 150. Dual separator 138 is configured as a single unit; alternatively as separate units. In certain instance, dual separator is configured to produce a separated stream 151. Separated stream 151 preferably comprises acetylene. Separated stream 151 is directed to hydrogenator 158. Hydrogenator 158 is configured to hydrogenate acetylene and produce olefinic stream 164, comprising ethylene.

$CO_2$ separator 140 is configured to remove $CO_2$ from the hydrocarbon portion of product stream 132. Further, the $CO_2$ separator 140 is configured for diverting $CO_2$ stream 142 to additional process. In certain instances, $CO_2$ stream 142 is directed to a $CO_2$ contaminant removal 144. $CO_2$ contaminant removal 144 is configured to isolate only $CO_2$ gas from any further gases, for instance carbon monoxide, hereinafter CO. $CO_2$ contaminant removal 144 creates $CO_2$ product stream 149. $CO_2$ product stream 149 may be used for other processes as understood by one skilled in the art. In certain instances, $CO_2$ product stream is directed at least partially to the fuel stream 121, to burner 120.

$CO_2$ contaminant removal produces a CO stream 146. CO stream 146 may be directed to the other processes. For instance, CO stream 146 is directed to a Fischer-Tropsch process 210, hereinafter, FT process 210. FT process 210 comprises an FT reactor 148. FT reactor 148 may comprise any reactor known by one skilled in the art to be used in an FT process 210. In certain instances, reactor is a syngas reactor, a hydrocarbon reactor, or a clarifying reactor. Without limitation, an FT process 210 produces an FT hydrogen stream 162 and an FT olefin stream 163. FT hydrogen stream 162 is directed to hydrogenator 158. In certain instances, FT olefin stream 163 is directed to olefinic stream 164 from hydrogenator 158.

Hydrocarbon separator 150 is configured to separate acetylene from ethylene and other olefins. In certain instances, hydrocarbon separator produces acetylene stream 151 that is directed to hydrogenator 158 and ethylene/olefin stream 152 directed to further processing and separation. Ethylene/olefin stream 152 is directed to ethylene purification 154. Ethylene purification 154 produces gas recycle stream 155 and ethylene stream 156. Gas recycle stream 155 comprises unreacted gases, exhaust gases, and hydrogen without limitation. Gas recycle stream 155 is directed to burner 120 via fuel stream 121. Ethylene stream 156 is directed to olefinic stream 164 from hydrogenator 158.

Hydrogenator 158 comprises any hydrogenation reaction known to one skilled in the art. In certain instances, hydrogenator 158 comprises a catalytic hydrogenator or a thermal hydrogenator without limitation. Hydrogenator 158 produces olefinic stream 164, preferably comprising ethylene. Olefinic stream 164 comprising hydrogenated acetylene from hydrogenator 158, FT olefin stream 163, and ethylene stream 156 is directed to a product finishing reactor 170. In certain instances, finishing reactor 170 is a liquid hydrocarbon reactor. Alternatively, product finishing reactor 170 serves as a mixer, to mix streams. Product stream 172 is directed to transport 175. In certain instances, final stream 172 is distilled, catalytically reacted, processed, mixed or otherwise refined into final products, product precursors, and derivatives without limitation, prior to transport 175.

Figure 6:
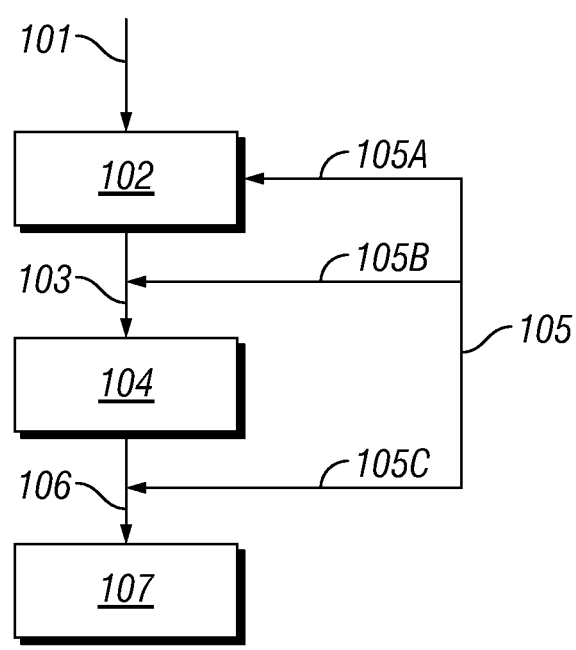
FIG. 6 shows an exemplary process diagram for the preparation of an externally hydrogen stream for implementation in a process of producing liquid hydrocarbons from natural gas.

Referring now to FIG. 6 that illustrates an exemplary method for forming and directing an externally derived hydrogen stream for incorporation into a liquid hydrocarbon production system 107, herein after system 107. Hydrogen source comprises a biomaterial, herein after BM. BM provides a biomaterial stream 101 to gasifier 102. Gasifier 102 produces hydrogen stream 106 for the system 107 via separator 104. Further, biomaterial stream 101 and gasifier 102 are subject to at least one treatment stream 105.

Biomaterial comprises biomass such as yard and/or landscaping waste, compost, corn stalks, wheat husks, crop waste, forestry/timber waste, sawdust, lumber scraps, and combinations thereof. BM comprises lignocellulose, pulp, pulping liquor, paper waste, and combinations thereof. Examples of other plant derived sources, include the husks, shells, and waste from biodiesel production or alcoholic beverage fermentation, brewing, distillation, and aging without limitation. Further, biomaterial may comprise farm slurries, poultry litter, cattle bedding/manure, pig bedding/manure, fishery dredgings, slaughterhouse waste, and the like without limitation. BM may comprise any organic waste, residues, or slurry derived from industrial processing of biological material for food stuffs, textiles, residues, polymers, and the like without limitation. Further, BM comprises coal and coal derivatives. BM comprises peat, lignite, sub-bituminous, bituminous coal, anthracite, and derivatives thereof. In instances, peat, lignite and sub-bituminous coals are preferred.

Biomaterial stream 101 comprises a slurry of biomaterial. Biomaterial stream 101 comprises BM that is mechanically sheared, chopped, ground, shredded, or the like to form a particulate mass. In certain instances, biomaterial stream 101 comprises a medium biomaterial grade, having a size of less than about 100 mm; alternately, the biomaterial stream comprises biomaterial fines, having a size of less than about 30 mm. Alternatively, the BM is pulverized to produce a particulate or powder. In certain instances, biomaterial stream 101 comprises a liquid, such as water or alcohol for at least partially suspending BM.

Biomaterial stream 101 is directed to a gasifier 102. Without limitation by theory, a gasifier 102 is configured to expose the BM to steam and oxygen under increased temperature and pressure. The reaction is configured to oxidize the BM to form a gas stream 103. Oxidized BM forms gas stream 103 comprising reactive components. In certain instances, gas stream 103 comprises hydrogen and carbon monoxide; alternatively "syngas." Additionally, gas stream 103 comprises methane, or natural gas, hereinafter NG. In further instances, gas stream 103 comprises coal gas, manufactured gas, pygas, illumination gas, or other forms of coal-derived gas without limitation. In certain instances, gas stream 103 comprises carbon dioxide, oxides of nitrogen, oxides of sulfur, and other volatile organic compounds, without limitation.

Gas stream 103 is introduced to separator 104 for separating a hydrogen stream 106 from other gas components. In certain instances, hydrogen stream 106 comprises a combustion stream; alternately, hydrogen comprises a reactant. In certain instances, hydrogen stream 106 is separated from other components for combustion. Without limitation by theory, combustion of hydrogen produces only water. Further, hydrogen will combust in air at concentrations between about 4% and 75% by volume. In certain instances, separator 104 comprises a means to separate hydrogen from all oxidizing compounds. Separator 104 is configured to produce a hydrogen stream having at least about 5% hydrogen. Hydrogen stream 106 is introduced to system 107.

At any point prior to introduction to a liquid hydrocarbon production system 107, hydrogen stream 106 is treated by a treatment stream 105. Alternatively, treatment stream 105 is introduced to gasifier 102 as gasifier treatment stream 105A, to gas stream 103 as gas treatment stream 105B, or to hydrogen treatment stream 105C. In instances, gasifier treatment stream 105A comprises chemical oxidants. In certain instances, gasifier treatment stream comprises an acid, for instance nitric acid, hydrochloric acid, or sulfuric acid. Without limitation by theory, treatment with acid reduces organic compounds in the BM and increases the hydrogen concentration within the BM prior to and during gasification. Additionally, gasifier treatment stream 105A comprises a BM upgrading composition, dewatering agent, or bleaching agent for removing water, salts, and certain pollutants found in the BM stream 101 during gasification. Further, the gas treatment stream 105B comprises water, steam, carbon monoxide, carbon dioxide, methane, ethylene, acetylene or another gas without limitation. In instances, gas treatment stream 105B is injected to increase the hydrogen concentration in the gas stream 103 from gasifier 102. Further, treatment stream 105 comprises a hydrogen treatment stream 105C. In instances, hydrogen treatment stream comprises a means of dewatering hydrogen stream 106. Alternatively, hydrogen treatment stream 105 comprises gases for stabilizing hydrogen stream 106 and preventing explosion, oxidation, or leaks. In certain instances, hydrogen treatment stream 105C comprises pollutant reducing compounds. Hydrogen treatment stream 105C may comprise certain compounds to control or alter the temperature of combustion of the hydrogen.

In certain instances, the BM stream 101 is fed to gasifier 102 which comprises a fermentative hydrogenation process. In instances, BM stream 101 and gasifier 102 comprise an anaerobic conversion process. Further, gasifier 102 comprises any fermentation apparatus as known to one skilled in the art, for instance, a digester. Gasifier 102 comprises a dark fermentation or a photo-fermentation processes, without limitation. Alternatively, gasifier 102 comprises a plurality of fermentation processes to maximize hydrogen production. Gasifier 102 comprises at least one microorganism derived enzyme system for producing hydrogen.

Alternatively, BM stream 101 comprises a syngas stream, for instance derived from a Fischer-Tropsch process. Fischer-Tropsch catalyzed reaction for production of liquid hydrocarbons may result in excess hydrogen, carbon monoxide, and other tail gases. The Fischer-Tropsch, hereinafter FT, process produces gas hydrocarbons. In instances, BM stream 101 comprising syngas, carbon monoxide, other tail gases and gas hydrocarbons, is passed through the gasifier 102, without further processing. Alternatively, a stream of FT syngas, carbon monoxide, tail gases, and the like may be directed to the gas stream 103. Further a stream of FT syngas, carbon monoxide, tail gases, and the like may be directed to the separator 104. After processing by separator 104 the hydrogen is introduced to hydrogen stream 106.

Hydrogen stream 106 may be derived from electrolysis of water. Electrolysis of water comprises various techniques known to one skilled in the art, such as Hofmann type electrolytic cells, high pressure electrolysis, or high temperature electrolysis, without limitation. In instances, the electrolysis of water is powered by an electrical source, such as steam turbine, nuclear powered, or solar. In further instances, the electrolysis of water uses a fuel cell, heat generated from burner 20, and steam for fuel feed 21, as illustrated in FIG. 5. Further, heat generated by a fuel cell may be used to boil the water exiting the fuel cell, forming steam. This steam maybe used to generate, electricity, for instance in a steam turbine, for the electrolysis of water to produce a hydrogen stream 106. In further instances, the electricity may be sold, or used to provide heat to preheat the feed, fuel or oxidant, or other equipment, such as, but not limited to, pumps, compressors, fans and other ordinary equipment required to accomplish the goals of the process.

In further alternate instances, the hydrogen stream 106 is derived from a carbon-black/plasma burner process, such as, but not limited to the Kvaerner process. In certain instances, a carbon source, such as carbon black is directed to a plasma burner with hydrocarbons such as, methane, natural gas, biogas, and the like, without limitation. In a Kvaerner process configuration, the gasifier 102 comprises the plasma burner and associated apparatus configured for the formation of hydrogen gas and solid carbon. In further instances, the hydrogen stream 106 is derived from any chemical or industrial process that electrolyzes, thermally decouples, or otherwise produces free hydrogen from a hydrogen containing molecule. In certain instances, a hydrogen containing molecule comprises a salt, an acid such as hydrogen chloride, a base, or the like, without limitation.

Referring again to FIG. 5, hydrogen stream 106 is directed to burner 120. Hydrogen burn stream 106A is derived from any externally derived hydrogen stream as discussed hereinabove. Without limitation by theory, the hydrogen burn stream 106A results in a burner temperature between about 2000K and about 3500K. In certain instances, hydrogen burn stream 106A enhances burner feed 121. Hydrogen burn stream 106A reduces the volume of burner stream 116, comprising NG. Reducing the volume of burner stream 116, increases the volume of NG available for conversion to liquid hydrocarbons, as hydrogen burn stream 106A replaces burner stream 116. Hydrogen burn stream 106A provides a means to increase liquid hydrocarbons. Hydrogen burn stream 106A increases efficiency of conversion.

Further, without limitation by theory, hydrogen in hydrogen burn stream 106A burns at an increased temperature compared to NG in burner stream 116. Hydrogen burn stream 106A produces an exhaust gas that has reduced pollutants, compared to combusting burner stream 116 comprising NG. In further applications, hydrogen in hydrogen burn stream 106A produces water as a result of combustion. Hydrogen burner stream 106A is mixed with oxygen enriched gases for improved combustion and reduced pollutants. Oxygen enriched gases may be included in hydrogen burner stream 106A. Alternatively, oxygen enriched gases may be introduced to burner 120 via fuel stream 121. Burner 120 is configured for at least the partial combustion of hydrogen. In certain applications, burner 120 partially combusts hydrogen in hydrogen burn stream 106A to form burner products stream 122. Additionally, unburned hydrogen burn stream 106A components in burner product stream 122 are introduced to reactor 130. Incompletely combusted hydrogen in burner product stream 122 increases the volume of hydrogen available for reactions.

In further applications, the hydrogen stream 106 is introduced to a Fischer-Tropsch process 110. The FT process 210 is configured to produce further hydrocarbons as discussed hereinabove. In certain instances, an FT hydrogen feed 106B is directed to FT process 210. FT hydrogen feed 106B is at least partially mixed with carbon monoxide to form syngas. FT hydrogen feed 106B configured for reacting in a catalytic production of hydrocarbons via FT olefin stream 163. Further, FT hydrogen stream 162 is formed as at least a portion of the products of FT reactor 148 and FT process 210. In certain instances, FT hydrogen stream 162 comprises hydrogen that passes through FT process without reaction. FT hydrogen stream 162 comprises tail-gases formed in FT reactor 148 of FT process 210. In certain instances, FT hydrogen stream 106B is passed through FT process 210 without reaction to form FT hydrogen stream 162. For example, economic factors may favor the temporary shut down of FT process 210. In certain configurations, FT hydrogen feed 106B is rerouted such the hydrogen feed 106B flows directly into FT hydrogen stream 162. Alternatively, FT hydrogen feed 106B is at least partially directed through FT process 210 and FT reactor 148, without reaction activity, conversion, or catalyzed processes, without limitation, to form FT hydrogen stream 162.

In alternative configurations, hydrogen stream 106 is introduced as a hydrogenation stream 106C. Hydrogenation stream 106C feeds hydrogenator 158 for the conversion of acetylene stream 151 to ethylene. Hydrogenator 158 is a reactor where alkynes, preferably acetylene, may be converted into a preferred intermediate product, preferably comprising ethylene and other olefins. The stream 151 comprising acetylene may be selectively subjected to hydrogenation in hydrogenator 151 by dual separator 138, specifically, by ethylene separator 150. Hydrogenator 158 forms olefinic stream 164, comprising ethylene. In certain instances, olefinic stream 164 comprises at least 5% ethylene by volume; preferably, 50% ethylene by volume; and in certain instances 75% ethylene by volume.

Olefinic stream 164 is directed to finishing reactor 170. Finishing reactor 170 comprises a catalytic liquefaction reactor that may include internal recycle and is designed to convert the outlet stream 164 to hydrocarbon liquids, such as naphtha or gasoline. The reactions in finishing reactor 170 to produce naphtha or gasoline are thermodynamically favorable, as equilibrium thermodynamics for the reactions of outlet stream 164 with hydrogen from FT hydrogen feed 162, hydrogenation stream 106C, and/or methane are more favorable at low to moderate temperatures (300°-1000°K). In instances, the hydrocarbons of olefinic stream 164 are converted to higher molecular weight hydrocarbons using acid catalysts, such as the zeolites H-ZSM-5 or Ultrastable Y (USY). The catalyzed hydrogenation in finishing reactor 170 is favorable to suppress the reaction of olefinic stream 164 components to benzene. The reaction is controlled to enhance the conversion of olefinic stream 164 to form product stream 172. Product stream 172 may be a liquid hydrocarbon stream comprising naphtha or gasoline. Product finishing reactor 170 preferably produces predominantly naphtha or gasoline, but may also produce some aromatic and cyclic compounds. The vapor pressure of naphtha or gasoline is about 1 bar (100 kPa) at 40° C.

The hydrocarbon liquid containing product stream 172 is processed for transport 175. Product stream 172 is processed for improved stability during transport 175. Product stream 172 is processed to remove catalyst particles, fines, and/or contamination prior to transport. Product stream 172 is mixed or blended with other compositions for improved refining at a remote location. For instance, heavier hydrocarbons such as crude oil may optionally be blended with the liquid products to reduce the vapor pressure of liquids for transport 175.

Although the present invention has been described with reference to specific details, it is not intended that such details should be regarded as limitations upon the scope of the invention, except as and to the extent that they are included in the accompanying claims.

I claim:

1. A method for converting natural gas to acetylene, comprising the steps of:
   producing a gaseous stream comprising hydrogen from an externally-derived process;
   separating externally-derived hydrogen from the gaseous stream;
   providing a stream of natural gas;
   forming a feed stream comprising a first portion of the natural gas stream, and a burn stream comprising a second portion of the natural gas stream, wherein the feed stream, the burn stream, or both further comprise at least a portion of the externally-derived hydrogen;
   conveying the burn stream to a combustion chamber, wherein the burn stream is at least partially combusted, to produce thermal energy;
   conveying the feed stream to a reactor, for reacting natural gas at a temperature for adequate time such that a product stream comprising acetylene is formed;
   quenching the product stream;
   removing acetylene from the product stream to form an acetylene product stream and a remaining portions stream comprising ethylene;
   separating the remaining portion stream into a combustion stream and a process stream;
   conveying at least a portion of the combustion stream to the combustion chamber, at least a portion of the process stream to the reactor, or both; and
   conveying the acetylene to storage or transport.

2. The method of claim 1, wherein providing a stream of natural gas further comprises removing contaminants.

3. The method of claim 1, wherein at least a portion of the thermal energy produced by combusting the burn stream heats the feed stream to at least about 1000K.

4. The method of claim 3, wherein the feed stream is heated to a temperature in the range from about 1000 K to about 1800 K for about 0.1 to about 100 milliseconds.

5. The method of claim 1, wherein conveying the feed stream to a reactor further comprises, preheating the feed stream.

6. The method of claim 1, wherein removing acetylene to form an acetylene product stream comprises isolating acetylene from ethylene.

7. The method of claim 1, wherein conveying the combustion stream to the combustion chamber further comprises introducing the combustion stream to the stream of natural gas, or the burner stream.

8. The method of claim 1, further comprising separating ethylene from the process stream to form a remainder product stream.

9. The method of claim 8, further comprising conveying at least a portion of the remainder product stream to the combustion chamber.

10. The method of claim 8, wherein separating ethylene further comprises at least one step selected from the group consisting of introducing the separated ethylene to the feed stream, introducing the separated ethylene to the reactor, introducing the separated ethylene to the product stream prior to quenching, introducing the separated ethylene to the product stream after quenching, and combinations thereof.

11. The method of claim 8, wherein the remainder product stream comprise one or more component selected from the group consisting of hydrogen, carbon monoxide, carbon dioxide, un-combusted natural gas, and combinations thereof.

12. The method of claim 11, further comprising
    separating hydrogen from the remainder product stream to form a hydrogen stream;
    conveying the hydrogen stream to a fuel cell or turbine; and
    reacting the hydrogen or burning the hydrogen in the turbine to produce electricity and heat.

13. The method of claim 12 further comprising directing electricity and heat to a preheater.

14. The method of claim 1 further comprising adjusting the quenching to minimize the concentration of ethylene in the product stream.

15. The method of claim 1, wherein the acetylene stream comprises at least about 5% by volume acetylene.

16. A method for converting natural gas to acetylene, the method comprising the steps of
    producing, from an externally-derived process, a gaseous stream comprising hydrogen;
    separating externally-derived hydrogen from the gaseous stream;
    providing a stream of natural gas;
    separating the natural gas stream to provide a feed stream and a burn stream, wherein the feed stream, the burn stream, or both further comprise at least a portion of the externally-derived hydrogen;
    conveying the burn stream to a combustion chamber, wherein the burn stream is at least partially combusted, to produce thermal energy;
    conveying the feed stream to a reactor, for reacting natural gas at a temperature for adequate time such that a product stream comprising acetylene is formed;
    quenching the product stream;
    removing acetylene from the product stream to form an acetylene stream and a remaining portions stream comprising ethylene;
    separating the remaining portions stream to form a combustion stream and a processing stream;
    directing at least a portion of the combustion stream to the combustion chamber; directing at least a portion of the processing stream to the reactor; or both; and
    conveying the acetylene stream for storage or transport.

17. The method of claim 16, wherein at least a portion of the thermal energy produced by combusting the burn stream heats the feed stream to at least about 1000K for about 0.1 to about 100 milliseconds.

18. The method of claim 16, wherein removing acetylene to form an acetylene product stream comprises isolating acetylene from ethylene.

19. The method of claim 16, further comprising isolating ethylene from the processing stream, and introducing the isolated ethylene to the feed stream, to the reactor, to the product stream prior to quenching, or a combination thereof.

20. The method of claim 16, wherein the product stream comprises at least about 70% by volume acetylene.

* * * * *